United States Patent [19]

Runge

[11] 4,004,299
[45] Jan. 25, 1977

[54] CARDIAC REPLACEMENT AND ASSIST DEVICES

[76] Inventor: Thomas M. Runge, 2501 Galewood Place, Austin, Tex. 78703

[22] Filed: Feb. 12, 1976

[21] Appl. No.: 657,703

[52] U.S. Cl. .................................. 3/1.7; 128/1 D; 92/31; 74/57
[51] Int. Cl.² ...................... A61F 1/24; A61M 1/03
[58] Field of Search ....... 3/1.7, 1; 128/1 D, DIG. 3; 92/31; 74/57

[56] References Cited

UNITED STATES PATENTS

| 1,921,235 | 8/1933 | Lindsey | 74/57 |
| 2,245,457 | 6/1941 | Brassell | 74/57 |
| 3,379,191 | 4/1968 | Harvey | 3/1.7 |
| 3,496,878 | 2/1970 | Hargest et al. | 3/1.7 X |
| 3,771,173 | 11/1973 | Lamb | 3/1.7 |
| 3,860,968 | 1/1975 | Shapiro | 3/1.7 |

FOREIGN PATENTS OR APPLICATIONS

| 94,306 | 6/1969 | France | 3/1.7 |

*Primary Examiner*—Ronald L. Frinks
*Attorney, Agent, or Firm*—B. P. Fishburne, Jr.

[57] ABSTRACT

In accordance with one embodiment of the invention, a total cardiac replacement device or four chambered heart for orthotopic placement is provided. This device is a pulsatile flow, synchronous ventricular ejection pump which closely simulates the action of the human heart. An internal electrical drive motor is powered by radio frequency induction across intact skin without external connections. A grooved rotary shaft driven by the motor powers a linear follower disc in one direction to compress two blood compatible sacs which simulate the left ventricle and right ventricle of the heart by pumping blood through the aorta and pulmonary artery, respectively. Return movement of the follower disc in terms of rate is a function of right atrial and left atrial pressure and volume. Stroke volume of each simulated ventricle is independent of the other, as in the natural heart. In a second embodiment of the invention, a left ventricle cardiac assist device shunts and pumps blood from the left atrium into the aorta while the recipient's natural heart is left intact. The assist device can also be utilized for pulmonary circulation as a right ventricular assist means, shunting and pumping blood from the right atrium into the pulmonary artery.

12 Claims, 13 Drawing Figures

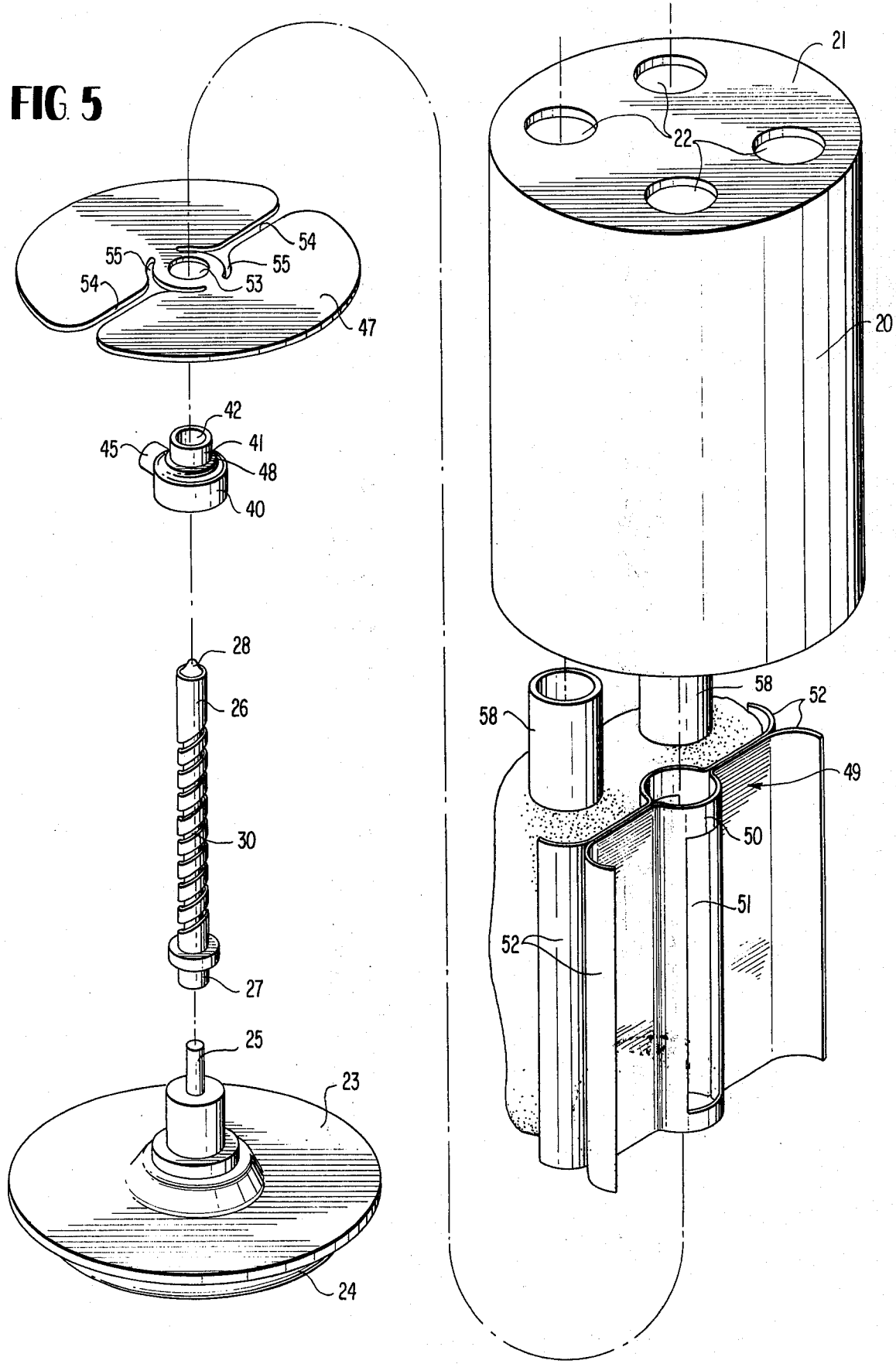

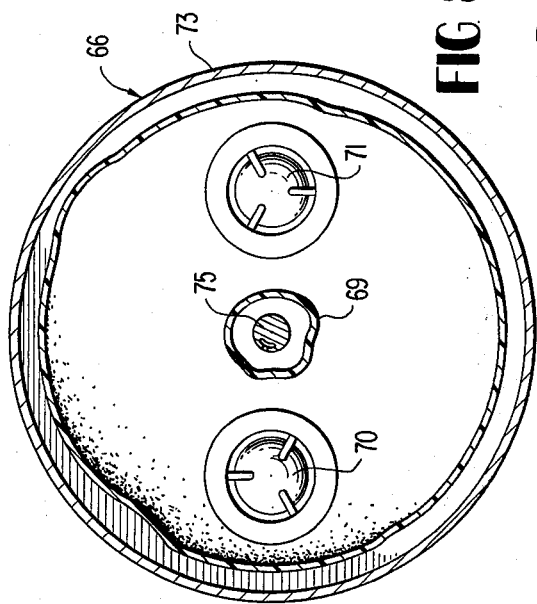
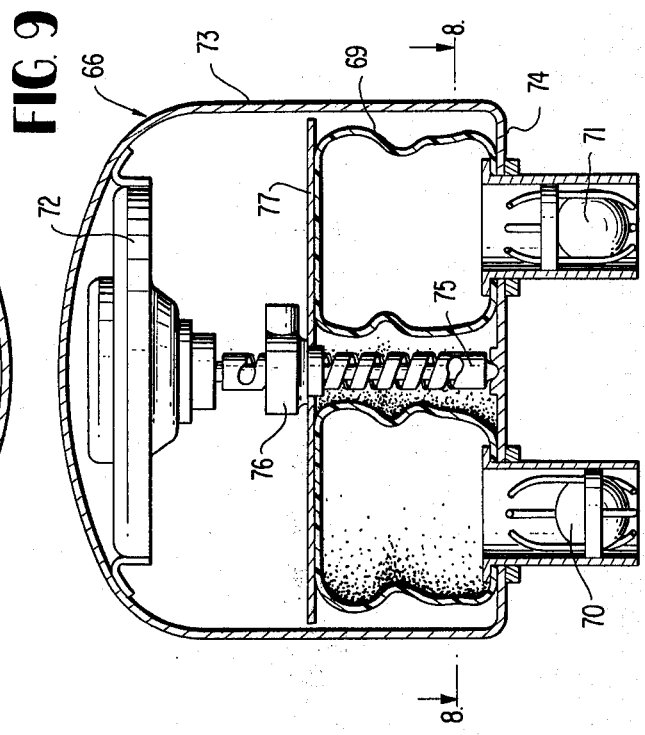
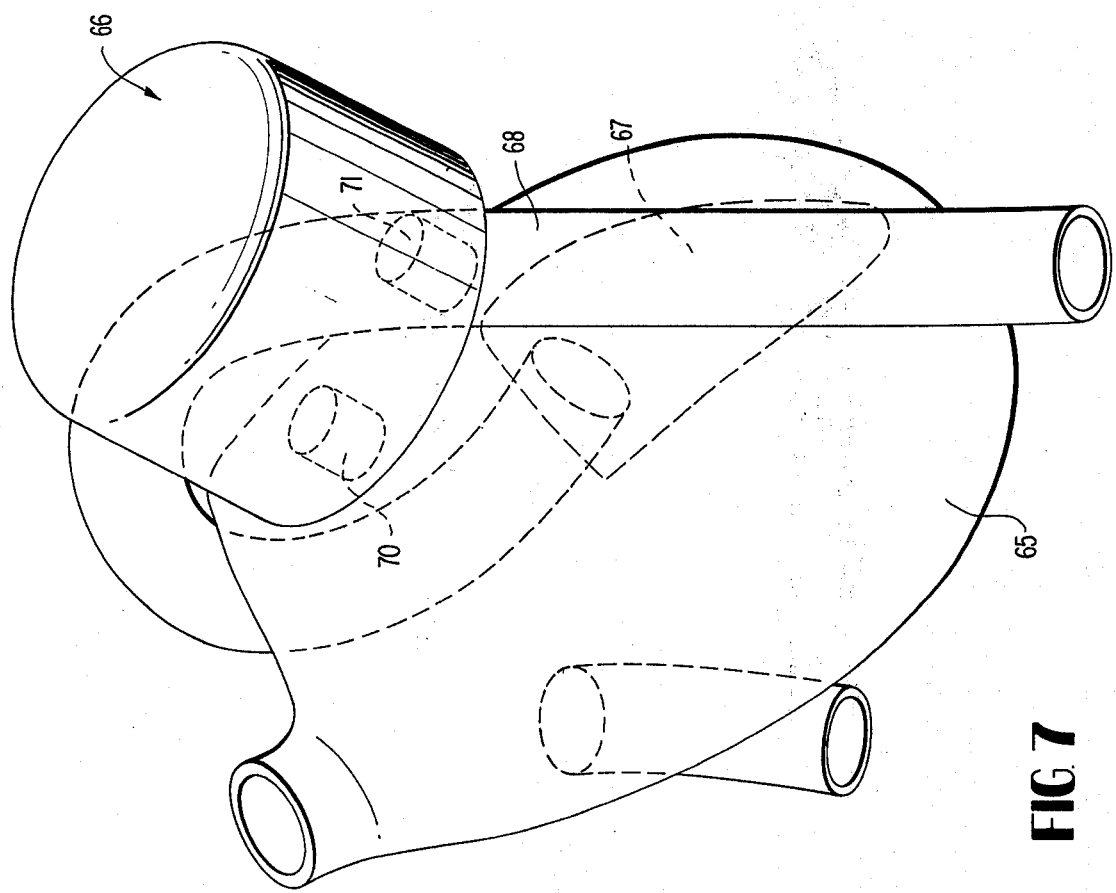

4,004,299

CARDIAC REPLACEMENT AND ASSIST DEVICES

BACKGROUND OF THE INVENTION

Recent dramatic advances in heart surgery have led to the feasibility of human heart transplant and to the realization that the eventual solution to the problem of replacing a failing human heart, or in assisting a failing heart, may lie in the use of a man-made cardiac replacement or assist device.

At the present time, machines are in use in hospitals to take over the function of the natural heart while surgery is being performed on the heart. There have also been some prior art proposals in terms of total cardiac replacement devices and assist devices, but up to now no such means suitable for human usage has been devised, although considerable research and development is being undertaken in this area.

The objective of this invention is to provide a device of the above-mentioned character which hopefully will advance the state of the art a step closer to the time when a man-made heart can be successfully employed inside of the body as a permanent replacement for a human heart which has failed. For such an event to become a reality, a large number of problems must be overcome including such factors as a practical long-lasting power supply, creation of a sufficiently compact, efficient and durable pumping mechanism, discovery of materials which are compatible with human blood and tissue, maintaining hemolysis within acceptable limits, and other known criteria. Substantial progress has been made and is being made toward the solutions of some of these problems while work continues in the medical and engineering communities toward developing an eventually successful device.

It is believed that the present invention constitutes a significant advance in the art by offering a solution to several of the known and as yet unsolved problems in the art. More particularly, the invention provides in one form a total cardiac replacement device and in a second form a left or right ventricular assist means which may be employed while the recipient's heart is left intact. In both forms, the operation of the invention simulates quite closely the activity or functioning of the natural heart in terms of providing for pulsatile flow of blood, synchronous ventricular ejection, filling rate of ventricular sacs being a function of right and left atrial pressure and volume, and independent stroke volume of each simulated ventricle. In the total cardiac replacement embodiment, the device simulates the natural four chambered human heart, while in the ventricular assist embodiment, a single chambered pumping means is employed. Both forms of the invention utilize caged ball-type check valves of a proven commercial design. In both embodiments of the invention, blood is contained in atrial and ventricular blood compatible sacs and does not contact metallic parts of the device.

Other features and advantages of the invention will become apparent during the course of the following detailed description.

BRIEF DESCRIPTION OF DRAWINGS

FIG. 5 is an exploded perspective view of the device with parts omitted for clarity.

FIG. 7 is a perspective view of a ventricular cardiac assist device according to a second embodiment of the invention.

FIG. 8 is a horizontal section taken on line 8—8 of FIG. 9.

FIG. 9 is a central vertical section taken through the assist device of FIG. 7.

DETAILED DESCRIPTION

Figure 1:
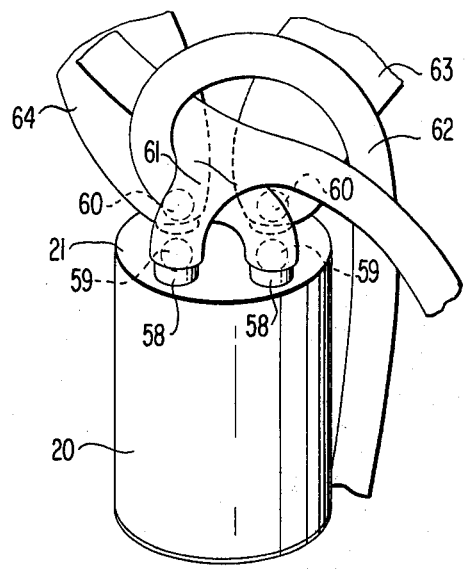
FIG. 1 is a partly schematic perspective view of a total cardiac replacement device according to one embodiment of the invention.
Figure 2:
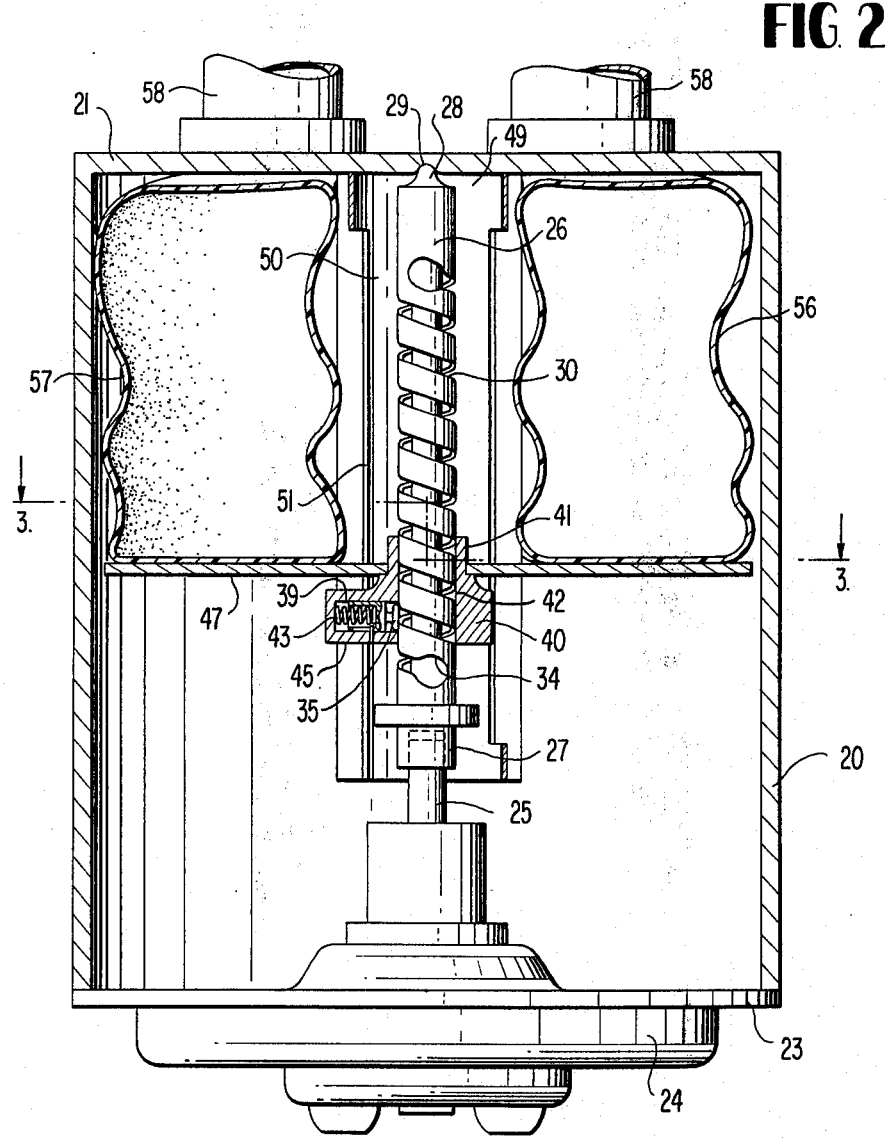
FIG. 2 is an enlarged central vertical longitudinal section through the device taken on line 2—2 of FIG. 3.
Figure 3:
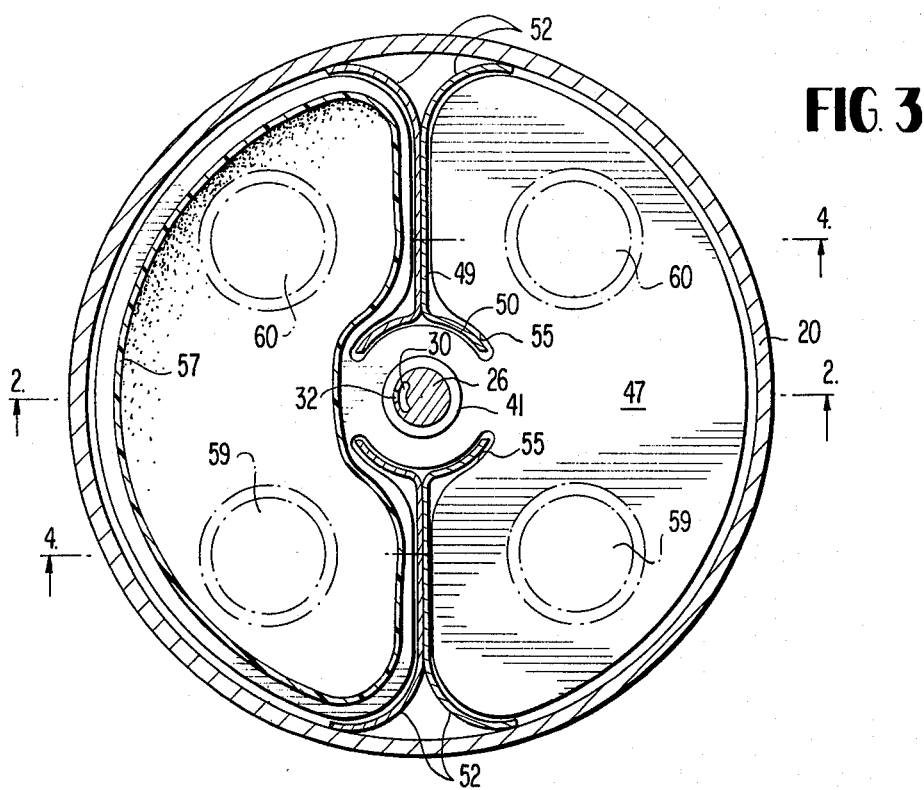
FIG. 3 is a horizontal section taken on line 3—3 of FIG. 2.

Referring to the drawings in detail wherein like numerals designate like parts and referring first to FIGS. 1 through 6d, a total cardiac replacement device or pump comprises a preferably cylindrical housing 20 including a top wall 21 having openings 22 formed therethrough for the placement of simulated heart valves, to be described, and their fittings. The lower open end of the housing 20 is closed in the assembled device by a circular plate portion 23 of a pancake electric motor 24, of a known type, having an armature or output shaft 25. The motor is adapted to be powered through radio frequency induction across the intact skin of the recipient from a primary external coil, not shown, to a secondary subcutaneous coil. Such powering means are known in the art and need not be described in detail herein. The motor plate portion 23 is fixedly attached to the housing 20 in the assembled device so that the motor armature shaft 25 turns relative to the stationary housing. The shaft 25 may be directly driven by the motor or driven through appropriate gearing.

A key element of the invention comprises a rotary grooved shaft 26 having a lower end extension 27 coupled to the motor shaft 25 and directly driven thereby. The upper end of rotary shaft 26 has a bearing tip 28 of spherical formation which revolves in a spherical bearing seat 29 of the housing top wall 21 for minimum friction.

The shaft 26 is provided over most of its length with a continuous constant pitch spiral groove 30 which is partially roofed at the cylindrical periphery of the shaft by continuous spiral opposing groove outer wall portions 31 forming between them an open continuous spiral passage 32 of somewhat restricted width.

Figure 6A:
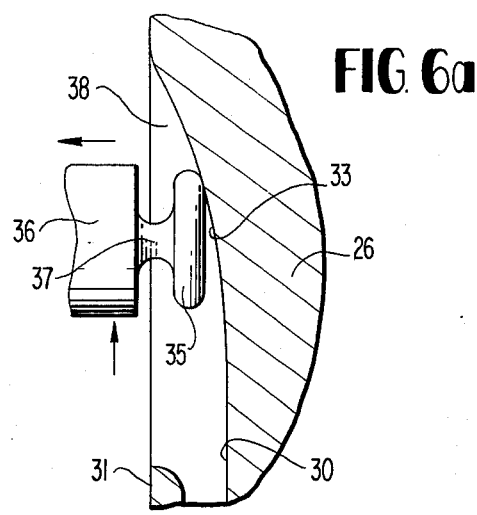
FIG. 6a is an enlarged cross section taken on line 6a—6a of FIG. 6.
Figure 6B:
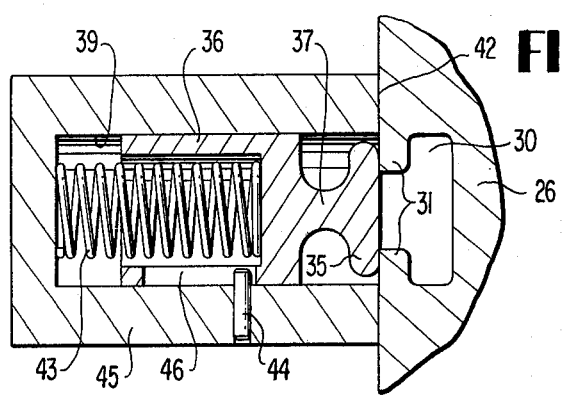
FIG. 6b is a similar fragmentary section taken on line 6b—6b of FIG. 6.
Figure 6C:
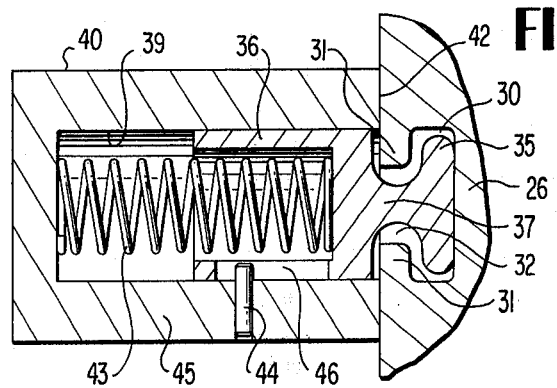
FIG. 6c is a similar view taken on line 6c—6c of FIG. 6.
Figure 6D:
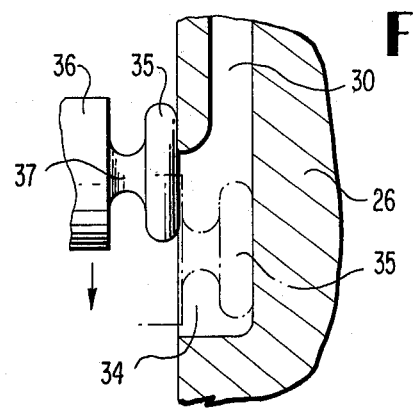
FIG. 6d is a similar view taken on line 6d—6d of FIG. 6.
Figure 6:
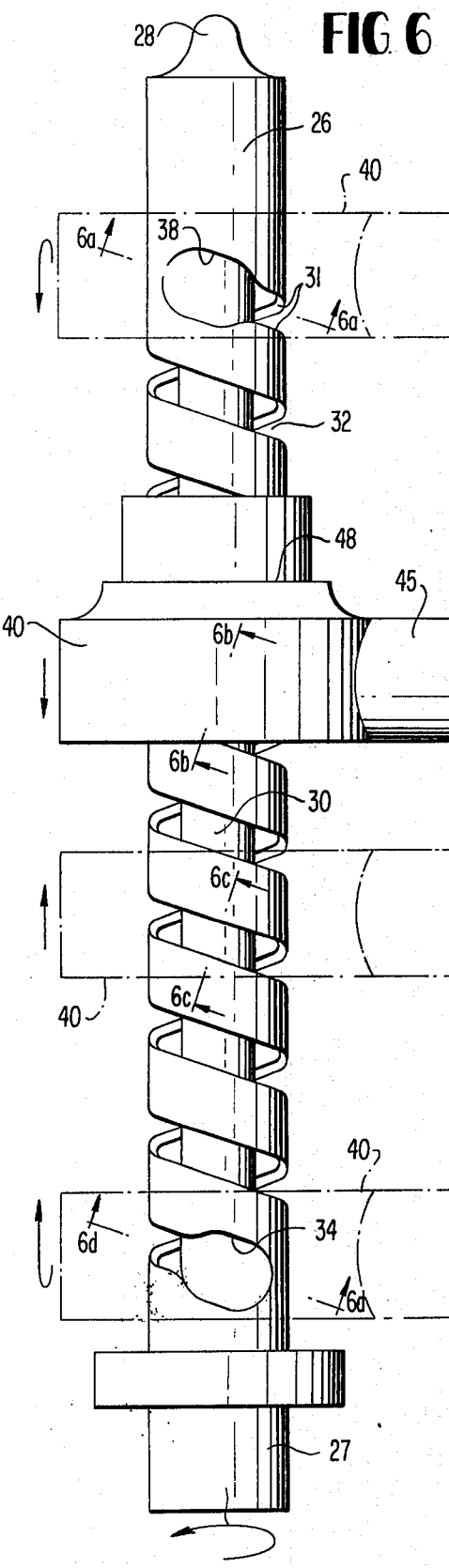
FIG. 6 is an enlarged side elevational view of a grooved rotary shaft and follower including a showing in phantom lines of various positions and directions of movement of the follower.

The spiral groove 30 is of uniform depth from its lower end near and above the coupling extension 27 to a point near its upper end, FIG. 6a, where the groove gradually and smoothly decreases in depth to zero along a curved surface 33. At its lower end, FIG. 6d, the spiral groove 30 has an enlarged entrance or mouth 34 for the entry of the head 35 of a spring-urged groove rider element 36 having a reduced diameter neck 37 immediately rearwardly of the head 35. Upon entry into the spiral groove 30 through the mouth 34, the head 35 is held captive in the spiral groove during upward travel therethrough as the shaft 26 revolves. At this time, the neck 37 of the rider element travels through the constricted spiral passage 32 during upward travel, as shown in FIG. 6.

Upon approaching the upper end of the groove 30, the rider head 35 encounters the curved groove wall 33 of diminishing depth and the rider element 36 is gradually forced toward the exterior of the shaft 26 and finally emerges through an upper enlarged exit opening 38 where the wall portions 31, forming the partial roof of the spiral groove, are not present, FIG. 6a.

Following disengagement from the spiral groove 30 near the top of rotary shaft 26, the follower element 36 begins to descend along the shaft 26 and its rate of descent and consequently the pumping rate of the device is a function of right atrial and left atrial pressure and volume, as will be further explained. As in the natural heart, the pumping rate will vary with ventricular filling pressure. During its descent along the peripheral surface of the shaft 26, the rider head 35 cannot reenter the groove 30 until it reaches the level of the entrance mouth or opening 34 where the groove is unroofed and the head 35 will then enter the groove 30 under spring pressure.

The rider element 36 which is cylindrical is contained within a bore 39 of a shaft follower bearing 40 having an upper sleeve extension 41 for added stability as the bearing slides along the periphery of rotary shaft 26. The follower bearing 40 has a main bore 42 at right angles to and intersecting with the rider receiving bore 39. An expansion spring 43 in the bore 39 constantly biases the rider element 36 forwardly toward the rotary shaft 26 assuring proper entry of the head 35 into the groove 30 at the mouth or entrance 34. The rider element 36 is held captive in the bore 39 and is restrained from rotating therein by a small pin 44 in the side extension 45 of follower bearing 40 which houses the rider element 36. The pin 41 is received in a longitudinal keyway slot 46 of the rider element 36, FIGS. 6b and 6c.

A ventricular sac compression disc or plate 47 rests upon a shoulder 48 of follower bearing 40 and moves upwardly and downwardly along the rotary shaft 26 with the follower bearing. The disc 47 is generally circular and spans most of the bore of housing 20, as shown. A housing divider and ventricular sac separator 49 is provided and fixedly attached to the top wall 21 of the housing, thus dividing the housing into simulated right and left ventricle compartments. The relatively stationary divider 49 has a center tubular portion 50 through which the shaft 26 projects and in which it operates. This portion 50 is slotted longitudinally at 51 to provide clearance for the radial extension 45 of follower bearing 40. The bore of tubular portion 50 is sufficiently large to receive the cylindrical body of the follower bearing 40. Curved flanges 52 on opposite sides of the plate-like divider 49 merely bear against the bore of housing 20 for stability. The disc 47 has a central opening 53 to receive the sleeve extension 41 of follower bearing 40 and is diametrically slotted as at 54 to receive the flat web portion of divider 49 for relative movement. The disc 47 also has arcuate slots 55 receiving the tubular portion 50 of divider 49 for relative movement.

Figure 4:
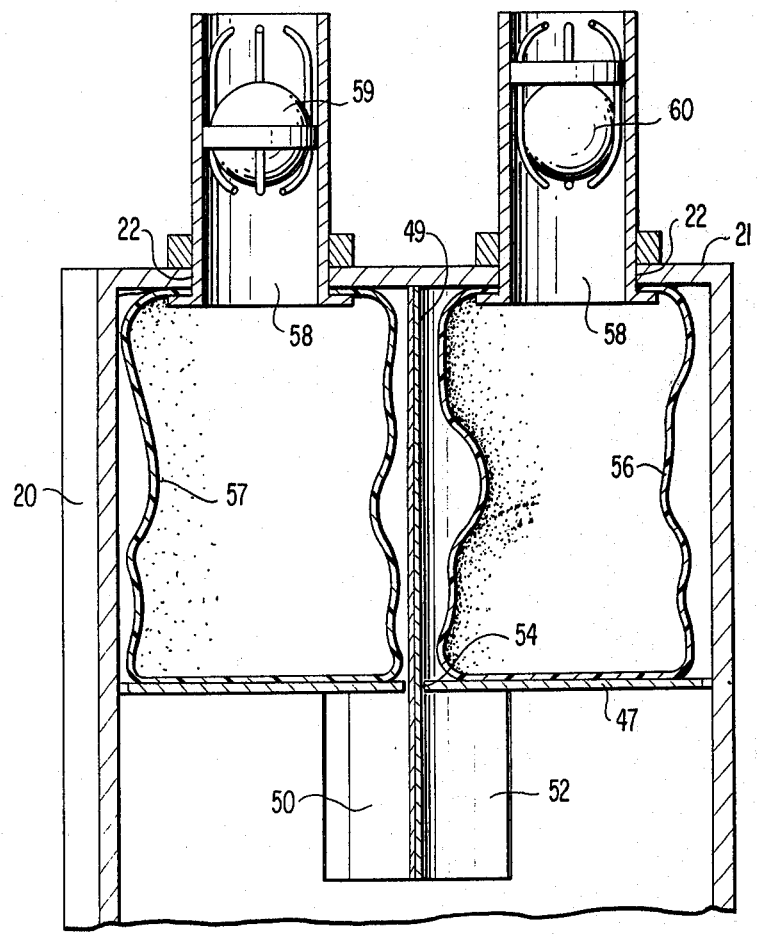
FIG. 4 is a fragmentary vertical section similar to FIG. 2 taken through the plane of simulated semilunar valves.

Left and right ventricle simulating pliable sacs 56 and 57 are arranged on opposite sides of the divider 49 within the housing 20 with their bottom walls resting on the disc 47. These sacs are formed from blood compatible material, such as Dacron reinforced Silastic or equivalent material. Each ventricular sac has a top outlet for blood and an inlet or return for blood, FIGS. 1 and 5. Each such connection is formed by a tubular fitting 58 within which is housed a conventional one-way closing and one-way opening caged ball-type check valve. One caged check valve 59 of each sac 56 and 57 is outwardly opening and thus represents the semilunar valve of the natural heart, FIGS. 1 and 4. The other caged valve 60 of each sac 56 and 57 is inwardly opening and outwardly closing and thus the valve 60 for the left ventricle sac 56 simulates the mitral valve of the natural heart and the valve 60 of the right ventricle sac 57 simulates the tricuspid valve of the natural heart. The illustration in FIG. 4 depicts the semilunar valve 59 of the right ventricle sac 57 and the mitral valve 60 of left ventricle sac 56. The four valves 59 and 60 are shown schematically in FIG. 1. In this figure, the pulmonary artery 61 is shown connected to the outlet 58 of the right ventricle sac 57 having the simulated semilunar valve 59, and the aorta 62 is connected with the outlet 58 of the left ventricle sac 56 having the other semilunar valve 59 therein.

Also, in FIG. 1, simulated left atrium and right atrium elements 63 and 64 are illustrated and these are formed from Dacron reinforced Silastic and are external to the housing 20. The elements 63 and 64 are adapted for attachment by known surgical methods to the pulmonary vein and superior vena cava, respectively, not shown. FIG. 1 also illustrates schematically the location of simulated mitral valve 60 and tricuspid valve 60 between the left atrium 63 and left ventricle sac 56 and between the right atrium 64 and right ventricle sac 57, respectively. The several tubular fittings 58 which house the ball-type check valves for the four chambered replacement heart are received within the four openings 22 in the top wall of housing 20.

SUMMARY OF OPERATION

With the pancake motor 24 operating continuously, the grooved shaft 26 will rotate at a predetermined constant speed. Assuming the two sacs 56 and 57 to be filled with blood and the disc 47 and follower bearing 40 to be in the full down position, the head 35 of rider element 36 will eventually register with the unroofed entrance 34 of spiral groove 30 and the rider spring 43 will force the rider head into the groove, as depicted in FIG. 6d. The coaction of the rider and spiral groove will immediately cause the follower bearing 40 and disc 47 to begin ascending the rotating shaft 26 and this action will begin the compression of the left and right ventricle sacs 56 and 57 forcing blood into the aorta 62 and pulmonary artery 61. The simulated semilunar valves 59 allow this pumping action which closely resembles natural heart action.

Eventually, the rider head 35 will encounter the gradually shallower face 33 of the spiral groove 30 near the top of shaft 26, and the face 33 will cam the rider 36 out of the unroofed exit 38 of the groove against the force of spring 43. At this point, the pumping stroke of the device has been completed.

Once the rider 36 is on the exterior of the shaft 26, it will begin its downward travel with the head 35 sliding on the periphery of the shaft 26 but unable to enter the groove 30 because of the partial roof forming wall portions 31. The rate of descent of the disc 47 and follower bearing 40 and hence the pumping rate of the device will vary with ventricular filling pressure. The rate of descent is a function of right atrial and left atrial pressure and volume, because the distention rate of the ventricular sacs 56 and 57 will vary with atrial pressure and volume.

The stroke volume of each simulated ventricle is independent of the other, as in the natural heart. The more taut (fuller) ventricle sac causes the disc 47 to descend, and therefore controls the pumping rate of the replacement heart. The other less taut or less full ventricle sac empties simultaneously. On the next cycle of operation, the situation could be reversed as to the relative tautness or fullness of the left or right ventricle sac 56 or 57 during descent of the follower bearing 40 and associated parts. It may now be understood that the overall action of the device closely resembles natural heart action.

During descent along the shaft 26, the rider head 35 will eventually again register with the unroofed mouth of the rider groove 30 and will pop into the groove entrance under influence of the spring 43 so that the pumping cycle may be repeated in the described manner.

In a second embodiment of the invention, FIGS. 7 to 9, the natural heart 65 remains intact and the device indicated generally by the numeral 66 is employed as an assist device rather than as a total replacement device. As illustrated in FIG. 7, the device 66 is serving as an assist device for the left ventricle 67 shown schematically in FIG. 7. The device shunts and pumps blood directly from the left atrium to the aorta 68. In some cases, the same device could be employed as a right ventricle assist device, in which case it would shunt and pump blood from the right atrium to the pulmonary artery.

The assist device 66 is constructed and operates similarly to the previously-described cardiac replacement unit. However, instead of employing two separate collapsible pumping sacs and four associated check valves, the assist device employs a single annular pumping sac 69 and a single pair of caged ball check valves 70 and 71, the latter allowing emptying of the sac 69 when the sac is compressed and the former allowing filling of the sac with blood. The materials employed for these parts and the basic drive mechanism remains the same as for the prior embodiment and need not be repeated in full detail.

However, the device 66 is mounted substantially upsidedown from the placement of the total cardiac replacement unit with the pancake-type electric motor 72 uppermost and near the top of a cylindrical housing 73 whose bottom wall 74 forms the support for the two valves 70 and 71 and their fittings. The motor 72 drives a grooved shaft 75 having an associated follower bearing 76 and rider, exactly as described in the prior embodiment in relation to FIGS. 6 through 6d. This detailed description need not be repeated. The mode of operation is the same except that the shaft 75 is reversed end-for-end from its position in FIG. 2 of the drawings and the associated disc 77 compresses the sac 69 downwardly instead of upwardly. On the reverse or filling stroke, the rate of ascent of the elements 66 and 67 and hence the pumping rate is again a function of atrial pressure and volume. As this pressure and volume rises, the Dacron Silastic sac 69 is filled and the follower bearing 76 is forced toward the motor 72 as the sac expands with the associated rider traveling along the exterior or periphery of the shaft. The rate of pumping is therefore related to filling pressure as in the prior embodiment. Other parts of the device 66 operate as previously described in connection with the first embodiment.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. A cardiac pumping unit comprising a housing, a motor connected with the housing, a rotary shaft coupled with the motor and driven thereby within the housing, said shaft having a spiral groove formed therein lengthwise and being partially roofed for the major portion of the length of the groove, said spiral groove having unroofed entrance and exit portions at its opposite ends and one end portion of the spiral groove diminishing gradually in depth adjacent one unroofed portion, a follower assembly on said rotary shaft including a spring-urged headed rider element for said spiral groove adapted to enter the groove at one unroofed portion and to leave the groove at the other unroofed portion while being cammed outwardly by the gradually diminishing depth of the groove adjacent the last-named unroofed portion, at least one pliable collapsible blood retaining sac in said housing, a disc element carried by the follower assembly and moving therewith along said rotary shaft in opposite directions to cyclically compress the sac for expelling blood therefrom followed by expansion of the sac to fill the same with blood, said follower assembly being positively driven axially on said shaft in the direction causing compression of the sac by interaction of the headed rider element and spiral groove, said follower assembly moving in the reverse axial direction on said shaft while the rider element is outside of the groove in response to filling blood pressure and volume in said sac, said partially roofed spiral groove preventing entry of the headed rider element into the groove between said unroofed entrance and exit portions, and a pair of oppositely acting one-way check valves connected with outlet and inlet means of the sac and housing.

2. A cardiac pumping unit as defined by claim 1, and a pair of separated right and left ventricle sacs in said housing each having associated outlet and inlet means for blood, and a pair of oppositely acting one-way check valves connected with said outlet and inlet means of each sac, whereby said pumping unit is adapted to serve as a total cardiac replacement device.

3. A cardiac pumping unit as defined by claim 2, and a relatively stationary divider within said housing between said pair of sacs and having a central tubular portion surrounding said rotary shaft, and said tubular portion being slotted longitudinally to receive a radially projecting part of the follower assembly.

4. A cardiac pumping unit as defined by claim 3, and said disc element having a central opening for engagement with a central portion of the follower assembly and being slotted diametrically and circumferentially to receive said divider and said tubular portion thereof for relative movement.

5. A cardiac pumping unit as defined by claim 1, and said follower assembly comprising a follower bearing having a main bore slidably receiving said rotary shaft and an intersecting radial bore, said spring-urged headed rider element mounted in said intersecting radial bore substantially perpendicular to the rotational axis of said shaft whereby the head of the rider element may abut and slide over the partially roofed portion of the spiral groove during descent of said follower assembly on said shaft.

6. A cardiac pumping unit as defined by claim 5, and an expansion spring mounted in said intersecting radial bore and engaging said headed rider to constantly urge it radially inwardly, said rider having a relatively narrow neck portion between its head and body and said neck portion adapted to travel through the partially roofed portion of said spiral groove.

7. A cardiac pumping unit as defined by claim 1, wherein said housing is substantially cylindrical and said pliable collapsible sac is an approximately annular sac surrounding said rotary shaft, said shaft being centrally disposed in said housing axially thereof, the arrangement being such that said pumping unit is adapted for use as a left or right ventricular assist device on an intact natural heart to shunt and pump blood from the left atrium to the aorta or from the right atrium to the pulmonary artery.

8. A cardiac pumping unit as defined by claim 1, and said motor being a pancake-type electric motor adapted for powering by radio frequency induction across intact skin, said motor having an armature shaft, said rotary shaft directly coupled to said armature shaft at one end of the rotary shaft, the other end of the rotary shaft having a bearing point for low friction rotation, and the housing having an end wall provided with a seating recess for said bearing point.

9. A cardiac pumping unit as defined in claim 2, and said housing comprising a substantially cylindrical housing having a diametrical divider wall means, and said pair of sacs disposed on opposite sides of the divider wall means and being roughly semi-cylindrical in configuration when in a filled state, and said disc element comprising a circular plate spanning substantially the interior of the cylindrical housing below said sacs.

10. A cardiac pumping unit as defined in claim 9, and said sacs as well as said check valves and said outlet and inlet means formed of non-metallic blood-compatible materials.

11. A cardiac pumping unit as defined in claim 10, and said sacs formed of Dacron reinforced Silastic.

12. A cardiac pumping unit as defined in claim 2, and an additional pair of sac-like elements external to said housing simulating the right and left atria and being operatively associated with one pair of said check valves which open inwardly in relation to said right and left ventricle sacs, whereby said pumping unit structurally and functionally resembles a natural four chambered heart.

* * * * *